United States Patent [19]

Taylor

[11] 3,962,137

[45] June 8, 1976

[54] PRODUCTION OF CO-CATALYST COMPOSITION OF INCREASED ABRASION RESISTANCE

[75] Inventor: Paul D. Taylor, Clinton, N.J.

[73] Assignee: Celanese Corporation, New York, N.Y.

[22] Filed: Nov. 25, 1974

[21] Appl. No.: 526,986

[52] U.S. Cl. .............................................. 252/456
[51] Int. Cl.² ...................... B01J 29/16; B01J 29/26
[58] Field of Search .................... 252/456, 459, 460

[56] References Cited
UNITED STATES PATENTS

| | | |
|---|---|---|
| 3,341,471 | 9/1967 | Callahan et al. ................. 252/456 X |
| 3,518,206 | 6/1970 | Sowards et al. ................. 252/456 X |
| 3,644,509 | 2/1972 | Allen .............................. 252/456 X |

*Primary Examiner*—Carl F. Dees

[57] ABSTRACT

The present invention provides a process for preparing a co-catalyst composition of increased abrasion resistance for use in reactions which involve reaction conditions of high stress, e.g., vapor phase oxidations. The process comprises intimately mixing an aqueous suspension of colloidal silica particles with a water-soluble metal salt which is decomposable by heat to a metal oxide, calcining the mixture, adding a further amount of the aqueous suspension of colloidal silica particles, and drying this co-catalyst composition.

4 Claims, No Drawings

PRODUCTION OF CO-CATALYST COMPOSITION OF INCREASED ABRASION RESISTANCE

BACKGROUND OF THE INVENTION

The use of chemical compositions as catalysts in reactions which involve reaction conditions of high stress, (such as high temperatures and pressures) requires a catalyst composition which is highly resistant to abrasion due to the deleterious effects of reaction conditions. For example, neat (i.e., unsupported) vanadium tetroxide has been used to catalyze the vapor phase oxidation of lower aliphatic hydrocarbons such as butane to acetic acid, but this "neat" catalyst lacks the physical strength and abrasion resistance requirements of a commercially acceptable catalyst.

This neat catalyst also lacks sufficient heat transfer characteristics for the highly exothermic vapor phase oxidation. Accordingly, hot spots are produced in the catalyst bed during the vapor phase oxidation.

In addition, when using neat vanadium tetroxide in the above reaction, it is necessary to maintain a careful balance between temperature and the ratio of lower aliphatic hydrocarbon to oxygen in order to prevent the neat catalyst from being oxidized to vanadium pentoxide.

Another problem which occurs when neat vanadium tetroxide is used as a catalyst for the vapor phase oxidation of lower aliphatic hydrocarbons is that substantially all (i.e., more than 75 percent) of the total conversion occurs in the first portion of the catalyst zone or bed (i.e., the first 25 percent of the total catalyst zone or bed) which is in contact with the reactants. This concentration of conversion in the first portion of the zone in an exothermic reaction raises the exotherm temperature at that point substantially in excess of that at later points in the catalyst zone. These high exotherm temperatures make control of the reaction more difficult, dictate more expensive heat-resistant materials, often increase the yield of undesirable by-products, and are otherwise disadvantageous.

Supported catalysts have been suggested as a means of overcoming some of the above problems. For example, in U.S. Pat. No. 3,644,509, which is assigned to the assignee of the present invention, there is disclosed an advantageous method for preparing a supported metal oxide containing catalyst useful in the vapor phase oxidation of unsaturated aldehydes to the corresponding acids.

The search has continued for high efficiency catalysts of increased physical strength and abrasion resistance which are useful in reactions involving conditions of high stress.

OBJECTS AND SUMMARY OF THE INVENTION

Accordingly, a general object of the present invention is to avoid or substantially alleviate the above problems of the prior art.

A more specific object is the provision of a process for producing an abrasion resistant catalyst.

A further object is the provision of a process for producing a catalyst having heat transfer characteristics which substantially alleviate hot spots in the catalyst bed during reactions such as vapor phase oxidations.

Still another object of the present invention is to provide a process for producing a catalyst for use in reactions such as vapor phase oxidations wherein a relatively even exotherm temperature may be maintained throughout the vapor phase oxidation reaction zone.

Still another object of the present invention is to provide such an abrasion resistant catalyst.

These and other objects are achieved by a process for preparing an abrasion resistant co-catalyst composition comprising a metal oxide and non-porous colloidal silica particles, which process comprises (a) intimately mixing an aqueous suspension of colloidal silica particles with an aqueous solution of a water-soluble metal salt which is decomposable by heat to a metal oxide, (b) calcining this mixture to form a metal oxide and non-porous silica containing co-catalyst composition, (c) adding further aqueous suspension of colloidal silica particles to the calcined co-catalyst composition of step (b), and (d) drying this composite co-catalyst.

The present invention also provides the co-catalyst composition prepared by this process.

The essence of the present invention is the formation of an outer porous net of non-porous colloidal silica particles over the calcined mixture of metal oxide and non-porous colloidal silica. This outer net tends to enhance the physical strength and abrasion resistance of the calcined mixture of metal oxide and non-porous colloidal silica so that the composition will retain its physical integrity even when subjected to conditions of high stress such as high temperatures and pressures.

Thus, this co-catalyst composition has greater physical strength than either neat metal oxide catalysts or metal oxide/silica catalyst mixtures which lack the outer porous net of non-porous colloidal silica particles which is formed in the process of the present invention.

Furthermore, the co-catalyst composition of vanadium tetroxide and finely divided, non-porous silica has been found to catalyze the oxidation of lower aliphatic hydrocarbons such as butane to acetic acid more efficiently than neat catalysts such as neat vanadium tetroxide. For example, in the vapor phase oxidation of lower aliphatic hydrocarbons such as butane to acetic acid, an increase in efficiency of nearly 10 percent (of theoretical yield) is realized when the co-catalyst composition of vanadium tetroxide and finely divided, non-porous colloidal silica particles of the present invention is used rather than neat vanadium tetroxide. In this connection, see copending U.S. patent application Ser. No. 526,659 which is hereby incorporated by reference and which describes in detail this particular vapor phase oxidation process.

Also, when the co-catalyst composition of vanadium tetroxide and finely divided, non-porous colloidal silica particles is used as catalyst for the vapor phase oxidation of butane to acetic acid, it is found that a relatively even exotherm temperature is maintained throughout the reaction zone. Further, this particular co-catalyst composition is comparatively insensitive to the balance of reactor temperature and the ratio of lower aliphatic hydrocarbon to oxygen.

Other objects and advantages of the present invention will become apparent from the following description of the preferred embodiments of the present invention.

DESCRIPTION OF THE PREFERRED EMBODIMENTS

The silica employed in the present invention comprises a colloidal suspension of an oxide of silicon in water. These aqueous colloidal silica sols are commercially available from, for example, the duPont Company under the tradename Ludox AS (ammonium stabilized).

The colloidal silica particles of the aqueous silica sols have a particle size of generally from about 0.001 to about 1.0, typically from about 0.005 to about 0.5, and preferably from about 0.01 to about 0.1 microns.

As indicated hereinabove, the non-porous colloidal silica is used in the process of the present invention both in step (a) and in step (c). Generally from about 30 to about 70, typically from about 40 to about 60, and preferably from about 45 to about 55 percent by weight of the total amount of the non-porous colloidal silica is added in step (a). The remainder of the silica is added in step (c).

The silica particles act as a heat sink which aids in the removal of heat from the catalyst as well as reduces the concentration of catalyst sites per volume. Thus, the same heat of reaction is spread over a larger volume than it would be if the metal oxide were not mixed with the silica. The aqueous colloidal silica suspension may be of widely varying proportions, although the silica particles are generally present at from about 2 to about 40, typically from about 6 to about 30, and preferably from about 10 to about 20 percent by weight of the total colloidal suspension and water is correspondingly present in an amount generally of from about 60 to about 98, typically from about 70 to about 94, and preferably from about 80 to about 90 percent by weight of the aqueous colloidal silica suspension.

Any metal salt the oxide of which is catalytically active in the ultimate process and which is both water-soluble and decomposable by heat to a metal oxide may be used to prepare the metal oxide employed in the present invention. Typical metal salts include the water-soluble oxalate salts of transition metals. A preferred transition metal containing salt is vanadyl oxalate. Vanadyl oxalate is both water-soluble and decomposes to vanadium tetroxide upon high temperature calcination.

The aqueous solution of the water-soluble metal salt may in general contain any proportion of water and metal salt as long as the solubility of the metal salt is not substantially exceeded. A high concentration of metal salt is generally preferred however in order to minimize evaporation. Thus generally the aqueous solution contains from about 2 to about 65, typically from about 20 to about 60, and preferably from about 40 to about 55, percent by weight metal salt and correspondingly may generally contain from about 35 to about 98, typically from about 40 to about 80, and preferably from about 45 to about 60, percent by weight water based upon the total weight of the aqueous solution.

The co-catalyst composition of metal oxide and non-porous colloidal silica may be of widely varying proportions, although metal oxide is generally present from about 25 to about 98, typically from about 50 to about 95, and preferably from about 65 to about 90, percent by weight of the total co-catalyst composition and the non-porous colloidal silica is correspondingly present in an amount of generally from about 2 to about 75, typically from about 5 to about 50, and preferably from about 10 to about 35, percent by weight of the total co-catalyst composition.

The co-catalyst particles produced in the process of the present invention will be larger than the individual non-porous colloidal silica particles because the colloidal silica particles tend to agglomerate when the catalyst composition is calcined. Thus, generally the co-catalyst particles will be larger than $10^{-7}$ centimeters (0.001 microns), typically from about $10^{-4}$ to about 2 centimeters. For example, when a fluidized bed reactor is used, particles of from about 0.001 to about 0.01, preferably from about 0.003 to about 0.008, centimeters are employed whereas when a fixed bed reactor is used, particles of from about 0.1 to about 1.5, preferably from about 0.2 to about 1.3, centimeters are employed. It will be understood that other shapes and sizes may be utilized depending upon the particular reaction, reactor, and reaction conditions.

Usually, the particles resulting from a given calcination will be a mixture of all sizes of co-catalyst particles. The calcined composition may be screened, sieved, or otherwise treated to segregate the mixture into co-catalyst particles of appropriate size, which size can be widely varied, as noted above.

These co-catalyst particles have a surface area of generally from about 20 to about 75, typically from about 30 to about 60, and preferably from about 40 to about 50 square meters per gram.

All steps of the present process except the calcining step (b) may be carried out at any temperature but generally a temperature of from about 20° to about 120°C, typically from about 25° to about 115°C, and preferably from about 30° to about 110°C is employed. The "calcining" step (b) in the present process may be carried out at temperatures generally greater than about 200°, typically greater than about 300°, and preferably greater than about 400° up to about 600°C. By "calcining" is meant prolonged heating at these high temperatures in an inert gas stream, e.g., nitrogen or other inert gases, in the substantial absence of oxygen.

The present process may be carried out at superatmospheric, atmospheric, or subatmospheric pressures but is generally carried out at about atmospheric pressure.

As indicated hereinabove, the co-catalyst composition of the present invention has a greater physical strength (or a greater "crush" strength) than that of a neat metal oxide catalyst. It has been found that neat metal oxide catalysts are extremely friable and tend to break apart under the conditions of certain reactions such as vapor phase oxidations. In contradistinction thereto, the particular composition of the present invention is extremely resistant to breaking or crumbling even at elevated temperatures and pressures.

In this specification, the term "abrasion resistance" is used to refer to the ability of the co-catalyst composition to retain its physical integrity when subjected to reaction conditions such as occur during high temperature and pressure vapor phase oxidations in a fluidized bed reactor. As catalyst particles rub against each other in such a reactor they tend to break apart in small particles or "fines". Abrasion resistance may be measured by the amount of fines coming out of the reactor in a unit time period.

By the term "crush strength" is meant the ability of the catalyst particles to withstand pressure without crumbling. Crush strength is measured in pounds per square inch per pellet.

Further, in this specification, the terms "conversion" and "efficiency" are defined as follows:

$$\text{Conversion, \%} = \frac{\text{moles reactant converted}}{\text{moles hydrocarbon reactant fed}} \times 100$$

-continued $$\text{Efficiency, \%} = \frac{\text{moles product}}{\text{theoretical moles product}} \times 100$$

Finally, by the term "contact time" is meant the contact time adjusted to 25°C and 1 atmosphere pressure (i.e., standard temperature and pressure, as denoted by STP). Thus the contact time is calculated by dividing the volume of the catalyst bed (including voids) by the volume per unit time flow rate of the reactants at STP.

The present invention is further illustrated by the following example. All parts and percentages in the example as well as in the specification and claims are by weight unless otherwise specified.

EXAMPLE I

This example illustrates the preparation of the co-catalyst composition of the present invention. This co-catalyst composition comprises vanadium tetroxide and non-porous colloidal silica.

The co-catalyst composition is prepared by dissolving 37.5 grams of vanadyl oxalate in enough water to bring the total volume to 70 milliters. 11 grams of an aqueous suspension of non-porous colloidal silica (containing 1.7 grams of non-porous colloidal silica particles having an average particle size of about 0.012 microns) is mixed with this solution in a Banbury mixer for about 15 minutes. This mixture is then dried for about 16 hours under nitrogen gas at 100°C and the solid is calcined in a 1-inch glass tube by heating initially at about 150°C for about 0.5 hours and then at about 400°C for about 4 hours in a nitrogen stream. This co-catalyst composition is allowed to cool at room temperature and is then removed from the calcining tube. At this point, another 11 grams of an aqueous suspension of non-porous colloidal silica (containing 1.7 grams of non-porous silica particles having an average particle size of about 0.012 microns) is added to the calcined co-catalyst composition. This composition is then dried at 120°C for 2 hours.

This procedure results in a co-catalyst composition comprising a porous net of non-porous colloidal silica on top of the lumps of calcined co-catalyst composition. The final co-catalyst composition contains about 90 weight percent of vanadium tetroxide and 10 weight percent non-porous colloidal silica. This catalyst composition is useful in reactions which involve high stress conditions.

EXAMPLE II

This example illustrates the differences between the catalyst of the present invention (catalyst A) prepared in Example I (above), neat vanadium tetroxide (catalyst B) and a catalyst composition of vanadium tetroxide and silica (catalyst C) which catalyst composition does not contain the porous net of non-porous silica as described herein.

Catalyst C is prepared by mixing an aqueous solution of vanadyl oxalate with sufficient porous silica particles to form, after drying and calcining, a 90/10 weight percent mixture of vanadium tetroxide and porous silica particles.

Each of catalysts A, B, and C has an average particle size of −20+30 mesh (about 500 to 775 microns).

Each catalyst is used in the vapor phase oxidation of butane to acetic acid in the presence of steam at a temperature of about 250°C for a contact time of 9 seconds (STP) at a butane to oxygen molar ratio of 5:1, and at a steam to butane molar ratio of 1:1. The reaction takes place at a pressure of about 1 atmosphere over a period of 36 hours.

On the basis of these runs, it is seen that when using the catalyst prepared by the process of the present invention, an increase in efficiency of nearly 10 percent (of theoretical yield) is realized over the other two catalysts. Also, the conversion based on butane is higher for that run wherein the catalyst of the present invention is employed.

Furthermore, the co-catalyst composition of the present invention (i.e., catalyst A) has a greater abrasion resistance and crush strength than that of either neat vanadium tetroxide (catalyst B) or the catalyst composition of vanadium tetroxide and silica (catalyst C) which catalyst does not contain the porous net of non-porous silica as described herein. The catalyst of the present invention has a crush strength almost twice as great as catalyst C and over five times as great as catalyst B. The abrasion resistance of catalyst A is almost twice as great as that of the other two catalysts. Finally, the absence of hot spots and the presence of a relatively even exotherm temperature throughout the reaction zone are characteristic of the co-catalyst composition of the present invention.

The principles, preferred embodiments, and modes of operation of the present invention have been described in the foregoing specification. The invention which is intended to be protected herein, however, is not to be construed as limited to the particular forms disclosed, since these can be regarded as illustrative rather than restrictive. Variations and changes may be made by those skilled in the art without departing from the spirit of the invention.

I claim:

1. A process for preparing an abrasion resistant, cocatalyst composition comprising vanadium tetroxide and non-porous colloidal silica particles, which process comprises (a) intimately mixing at a temperature of from about 25° to about 115°C an aqueous suspension which comprises from about 6 to about 30 percent by weight non-porous colloidal silica particles and from about 70 to about 94 percent by weight water with an aqueous solution of vanadyl salt which comprises from about 20 to about 60 percent by weight vanadyl salt and from about 40 to about 80 weight percent water, (b) calcining this mixture at a temperature greater than about 300°C to form a vanadium tetroxide and non-porous colloidal silica containing co-catalyst composition, (c) adding at a temperature of from about 25° to about 115°C an aqueous suspension which comprises from about 6 to about 30 percent by weight non-porous colloidal silica particles and from about 70 to about 94 percent by weight water to the calcined co-catalyst composition of step (b), and (d) drying this composite co-catalyst at a temperature of from about 25° to about 115°C, wherein in said process from about 30 to about 70 percent by weight of the total amount of the non-porous colloidal silica is added in step (a) and correspondingly from about 70 to about 30 percent by weight of the total amount of the non-porous colloidal silica is added in step (c).

2. A process for preparing an abrasion resistant, co-catalyst composition comprising vanadium tetroxide and non-porous colloidal silica particles, which process comprises (a) intimately mixing at a temperature of from about 30° to about 110°C an aqueous suspension which contains less than the total amount of non-porous colloidal silica particles ultimately added to form a co-catalyst composition, with an aqueous solution of vanadyl oxalate, (b) calcining this mixture at a temperature greater than about 400°C and up to about 600°C in a nitrogen gas stream to form a vanadium tetroxide and non-porous colloidal silica containing co-catalyst composition, (c) adding at a temperature of from about 30° to about 110°C an aqueous suspension which comprises the balance of the nonporous colloidal silica particles, and (d) drying this composite co-catalyst at a temperature of from about 30 to about 110°C wherein the final co-catalyst composition contains from about 65 to about 90 percent by weight vanadium tetroxide and correspondingly from about 10 to about 35 percent by weight non-porous colloidal silica based on the total weight of the co-catalyst composition, wherein in said process from about 30 to about 70 percent by weight of the total amount of the non-porous colloidal silica is added in step (a) and correspondingly from about 70 to about 30 percent by weight of the total amount of the non-porous colloidal silica is added in step (c).

3. The product of the process of claim 1.
4. The product of the process of claim 2.

* * * * *